United States Patent [19]

Romera et al.

[11] Patent Number: 5,789,646
[45] Date of Patent: Aug. 4, 1998

[54] PROCESS FOR THE PURIFICATION OF MEDIUM-CHAIN OLEFINS

[75] Inventors: Eric Romera, Kraainhem; Christian Lamotte, Arquennes; Philippe Bodart, Engis, all of Belgium

[73] Assignee: Fina Research S.A., Feluy, Belgium

[21] Appl. No.: 752,130

[22] Filed: Nov. 20, 1996

Related U.S. Application Data

[63] Continuation of Ser. No. 322,245, Oct. 12, 1994, abandoned.

[30] Foreign Application Priority Data

Oct. 15, 1993 [EP] European Pat. Off. ............ 093870202

[51] Int. Cl.$^6$ .................................. C07C 7/00; C07C 7/48
[52] U.S. Cl. .......................... 585/833; 585/520; 585/664; 585/666; 585/667; 585/670; 585/800; 585/851; 585/852
[58] Field of Search ................................ 585/520, 664, 585/666, 667, 670, 800, 833, 851, 852

[56] References Cited

U.S. PATENT DOCUMENTS

| 2,421,229 | 5/1947 | Zimmerman | 203/29 |
|---|---|---|---|
| 2,428,516 | 10/1947 | Drenna | 585/664 |
| 3,920,765 | 11/1975 | Frech et al. | 585/667 |
| 4,527,004 | 7/1985 | Sweeney | 585/851 |
| 4,547,780 | 10/1985 | Wilson | 585/377 |
| 5,132,484 | 7/1992 | Gajda | 585/667 |
| 5,237,120 | 8/1993 | Haag et al. | 585/666 |

FOREIGN PATENT DOCUMENTS 934783  8/1963  United Kingdom.

*Primary Examiner*—Elizabeth D. Wood
*Attorney, Agent, or Firm*—Michael J. Caddell; M. Norwood Cheairs; William D. Jackson

[57] ABSTRACT

Medium-chain olefins containing as impurities 2-alkyl substituted isomers having a close boiling point are purified by (i) passing over a solid acid catalyst under mild conditions to selectively double-bond isomerise said impurities, and (ii) separating said isomerised olefins by distillation.

12 Claims, No Drawings

PROCESS FOR THE PURIFICATION OF MEDIUM-CHAIN OLEFINS

CROSS REFERENCE TO RELATED APPLICATION

This application claims priority of a pending application filed in Belgium on Oct. 15, 1993, Ser. No. 93870202.4. This is a continuation application of U.S. Ser. No. 08/322,245, filed Oct. 12, 1994 and now abandoned.

BACKGROUND OF THE INVENTION

The present invention relates to the purification of medium-chain olefins, more particularly of medium chain alpha-olefins.

Industrial purification of medium-chain olefins is usually performed by distillation. However, certain isomers, particularly the 2-ethyl substituted alpha-olefins, do not have a boiling point sufficiently different from that of the alpha-olefin to be purified, and distillation is thus not fully efficient. For example, 2-ethyl-1-pentene has a boiling point of 94° C. while 1-heptene has a boiling point of 93.6° C.

Medium-chain alpha-olefins find many uses in industry. The most important ones are the synthesis of alcohols or aldehydes by hydroformylation ("oxo synthesis"), the production of synthetic lubricants by oligomerisation, and the production of copolymers with short-chain olefins.

For such uses, 2-alkyl substituted alpha-olefins can be an undesired impurity in the linear alpha-olefin whenever it is capable of reacting to give undesired side effects or side products. For example, aldehydes obtained by oxo synthesis can be converted into synthetic fatty acids which are used in the production of lubricants; however, lubricant production requires highly linear acids.

There is thus a need in the art for a process for the purification of medium-chain alpha-olefins, by removing therefrom the undesired isomers, particularly those that cannot efficiently be removed by distillation.

GB-934738-A and FR-2250729 disclose processes for the isomerization of tertiary olefins, respectively on pre-treated acid silica-alumina having ion exchange characteristics and on sulfonated ion exchange resins.

However, U.S. Pat. No. 5,237,120-A is evidence that conversion of 1-olefins to 2-olefins is obtained by double-bond isomerization on a zeolite whose surface has been at least partially deactivated for acid-catalyzed reactions.

It is an object of this invention to provide a process for the purification of medium-chain alpha-olefins.

Another object of the invention is to remove from medium-chain alpha-olefins the isomer 2-alkyl substituted alpha-olefins.

Still another object of the invention is to remove from medium-chain alpha-olefins those isomers whose boiling point is very close to that of said alpha-olefins.

Yet another object of the invention is to selectively double-bond isomerize 2-alkyl substituted alpha-olefin feeds into isomers having a lower reactivity with regard to that of the alpha-olefin in their later use.

SUMMARY OF THE INVENTION

It has now been found possible to purify medium-chain alpha-olefins by removing therefrom those 2-alkyl substituted isomers contained as impurities, particularly those having a boiling point very close to that of said alpha-olefins.

Accordingly, the present invention provides a process for the purification of a medium-chain alpha-olefin containing at least one isomer 2-alkyl alpha-olefin by removing therefrom the isomer 2-alkyl substituted alpha-olefin, said process comprising the steps of:

(i) providing a feed of medium-chain linear alpha-olefin containing one or more impurities, at least one of which is an isomer 2-alkyl substituted alpha-olefin;

(ii) passing said feed over a solid acid catalyst under mild conditions to selectively double-bond isomerize said isomer;

(iii) optionally, separating said isomerized olefin by distillation; and (iv) recovering a feed of medium-chain linear alpha-olefin essentially free of isomer 2-alkyl substituted alpha-olefin.

DESCRIPTION OF THE PREFERRED EMBODIMENTS

The present invention applies to medium-chain alpha-olefins. As used herein, medium-chain refers to a chain of five to eight carbon atoms, particularly seven. The feed should preferably be dry.

Although it may not be possible to apply the process of the invention to certain 2-alkyl substituted isomers, such as e.g. 2,3,3-trimethylbutene, when present as impurity, they generally have a boiling point such that they can be separated from the linear isomer medium-chain alpha-olefin by distillation.

Also, depending on the later use of the feed, the selective double-bond isomerization of a 2-alkyl substituted alpha-olefin present as impurity may be sufficient.

In other words, the resulting isomerised olefin, which is mainly a methyl-substituted non-terminal olefin, may be left in the feed whenever its presence as impurity does not cause any inconvenience, the distillation step then only not being required. (This will e.g. be the case when the reactivity of the isomerized olefin will be sufficiently low with regard to that of the alpha-olefin when later used.

In certain cases (e.g. 2-ethyl 1-hexene impurity in 1-octene), the boiling points (in the example : n-octene: 121.3° C., 2-ethyl 1-hexene: 120.0° C., 3-methyl 2-heptene: 122.0° C.) are such that a distillation step is of little use, and the process of the invention is thus in those limited cases only useful if the double-bond isomerised impurity (in the example: 3-methyl 2-heptene) can be left in the feed.

The invention is based on a process for the selective double-bond isomerisation of 2-alkyl alpha-olefins in the presence of the medium-chain linear alpha-olefin having the same number of carbon atoms. Although catalysed isomerisation of pure olefins appears to be known per se, the Applicant has found that by passing a feed of medium-chain linear alpha-olefin containing at least one isomer 2-alkyl substituted alpha-olefin as impurity over a solid acid catalyst under mild conditions, double-bond isomerisation of the impurity occurred with an unexpected selectivity.

Selectivity, as used herein in connection with this invention, refers to (i) an essentially total conversion of the 2-alkyl substituted alpha-olefin, with a very good conversion into the double-bond isomer, and (ii) essentially no conversion of the medium-chain linear alpha-olefin. Indeed, the yield of double-bond isomer is not critical in such a process, because the important factors are the residual amounts of medium-chain linear alpha-olefin (which should be as high as possible) and of 2-alkyl alpha-olefin (which must be as low as possible).

The process of the present invention requires a solid acid catalyst. In view of the diversity of solid acid catalysts, it is not possible to give ranges on an acidity scale. Catalysts having an excessive acidity will tend to yield adverse results (e.g. oligomerisation and/or isomerisation of linear alpha-olefins, oligomerisation of 2-alkyl alpha-olefins), while catalysts having an insufficient acidity will not be sufficiently active. Thus, the only possible way is to provide a very simple screening test which will allow a check on whether a solid acid catalyst is appropriate for the process of the invention; an acceptable catalyst should meet both of the following tests under the selected reaction conditions (as hereinafter described) using pure feeds:

(i) more than 95%, preferably more than 99%, conversion of the pure 2-ethyl substituted alpha-olefin, preferably with more than 80% (most preferably more than 90%) of the products being the 3-methyl 2-olefin double-bond isomer; and (ii) less than 3%, preferably less than 1%, conversion of the pure linear alpha-olefin.

Preferred catalysts include (i) non-fluorinated cross-linked sulphonic resins, and (ii) zeolites with pore openings having a diameter greater than 0.5 nm, preferably silicoaluminates having Si/Al atomic ratio in the zeolite skeleton of between 10 and 100, both under acid form.

Such zeolites can be, as usual in the art, formed into the desired shape in the presence of a binder (e.g. alumina or silica-alumina) which may represent up to 90 wt% of the catalyst (usually less than 30%).

As most preferred catalysts, we may cite Amberlyst 15 (Amberlyst is a trade mark) or HZSM-5 (i.e. Mobile Company ZSM-5 under acid form). The selective isomerisation should be performed under mild conditions. Such conditions comprise low temperature, e.g. from −10° C. to +50° C., preferably from 20° to 30° C. The isomerisation reaction itself appears to be relatively independent of the temperature, but side-reactions involving the medium-chain linear alpha-olefin appear to increase with temperature. Isomerization should be performed at atmospheric pressure, although lower or higher pressures could be used (e.g. from 0.01 to 1 MPa or even higher, with the proviso that it is preferable to operate in the liquid phase). Relatively high liquid hourly space velocities (LHSV) can be used with typical values ranging from LHSV=1 to 50 l/lh; and preferred values of LHSV of from 10 to 20 l/lh. Conditions differing from the above may be selected providing the catalyst passes the above-mentioned two tests under the selected conditions.

Should the activity of zeolite catalysts be found to have decreased, they may be reactivated either by treatment under hydrogen, optionally in the presence of methane or an inert gas, or by calcination under oxygen-containing gaseous stream, in both cases at a temperature of from 400° to 700° C.

Should the activity of resin catalysts be found to have decreased, they may be reactivated either by washing with a non-olefinic organic solvent, preferably of the alkane type, at a temperature below 150° C. or the boiling temperature of that solvent, whichever is lower, or by washing with a strongly acidic solution (e.g. pH=0).

The process of the invention also features an optional distillation step to separate whenever required the isomerized impurities from the feed. Such distillation step is conventional and need not be described further. The use of a simple distillation is now possible (except e.g. for separating n-octene and 3-methyl 2-heptene, as stated above) because the boiling point of the isomerised product is markedly different from that of the linear alpha-olefin (e.g. 3-methyl 2-hexene: 95.2° C. for the trans isomer, predominantly produced, and 97.3° C. for the cis isomer).

The invention can further be illustrated by the following examples:

EXAMPLE 1
purification of 1-heptene over HZSM-5
A feed of 1-heptene containing 1% of 2-ethyl 1-pentene was passed over HZSM-5 catalyst.
Under the following reaction conditions were selected for the isomerisation step:
temperature: 30° C.
pressure: 0.1 MPa (atmospheric)
LHSV: 10 l/l.h
The catalyst was ZSM-5 (silicon/aluminium atomic ratio in the zeolite skeleton : nominal=25, by 29Si NMR=29), deposited on alumina binder (80 wt% ZSM-5 on 20 wt% alumina) and extruded as 1/16" (1.6 mm) diameter pellets having a length of about 4mm. It was used under acid form (better known as HZSM-5) activated at 110° C. under nitrogen. The isomerization gave the following results:
(i) conversion of 2-ethyl 1 -pentene : more than 95%
(ii) conversion of 1-heptene : less than 2%
The resulting product was thereafter submitted to distillation, resulting in recovery of about 99% of the 1-heptene, which contained less than 0.01% of 2-ethyl 1-pentene as as impurity.

EXAMPLE 2
purification of 1-heptene over Amberlyst 15
Example 1 was repeated, except that Amberlyst 15 (1 mm diameter beads, rinsed three times with ethanol then 3 times with heptene; Amberlyst is a trade mark of Rohm & Haas) was used as catalyst. The results were essentially identical.

EXAMPLES 3 and 4
purification of 1-hexene
Examples 1 and 2 were repeated, except that 1 -hexene and 2-ethyl 1 -butene were used. The results were essentially identical.

We claim:
1. The process for the purification of a medium-chain linear alpha-olefin containing at least one isomer 2-alkyl alpha-olefin by removing therefrom said at least one isomer 2-alkyl alpha-olefin, said process comprising the steps of:
(i) providing a feed of medium-chain linear alpha-olefin containing one or more impurities at least one of which is an isomer 2-alkyl alpha-olefin;
(ii) passing said feed over a solid acid catalyst under mild conditions to selectively double-bond isomerize said isomer; and,
(iii) recovering a product stream of medium-chain linear alpha-olefin essentially free of isomer 2-alkyl alpha-olefin.

2. The process according to claim 1 further comprising the step of separating step (ii) - the isomerized olefin by distillation.

3. The process according to claim 1 wherein the mild conditions comprise a temperature of from +20 to +30° C., a pressure equal to atmospheric pressure, and a linear space velocity of from 10 to 20 l/lh.

4. The process according to claim 1, wherein the solid acid catalyst is selected so that, when tested under the reaction conditions, it converts less than 3% of the medium-chain linear alpha-olefin, and it converts more than 95% of the 2-ethyl alpha-olefin isomer.

5. The process according to claim 4, wherein the solid acid catalyst is selected so that, when tested under the reaction conditions, it converts less than 1% of the medium-chain linear alpha-olefin and it converts more than 99% of the 2-ethyl alpha-olefin isomer.

6. The process according to claim 1, wherein the solid catalyst is a non-fluorinated acidic cross-linked sulphonic resin.

7. The process according to claim 6, wherein the resin is reactivated by washing with a non-olefinic solvent.

8. The process according to claim 6, wherein the resin is reactivated by washing with a strongly acidic solution.

9. The process according to claim 1, wherein the solid catalyst is an acidic zeolite with pore openings having a diameter greater than 0.5 nm.

10. The process according to claim 9, wherein the zeolite catalyst is a silicoaluminate with Si/Al atomic ratio of the zeolite skeleton comprised between 10 and 100.

11. The process according to claim 10, wherein the solid catalyst after use is reactivated by treatment under H2, optionally in the presence of methane or an inert gas, at a temperature of from 400° C. to 700° C.

12. The process according claim 10, wherein the solid zeolite catalyst is reactivated by calcination under an oxygen containing gaseous stream at a temperature of from 400° C. to 700° C.

* * * * *

UNITED STATES PATENT AND TRADEMARK OFFICE
CERTIFICATE OF CORRECTION

PATENT NO. : 5,789,646
DATED : August 4, 1998
INVENTOR(S) : Eric Romers, Christian Lamotte and Philippe Bodart It is certified that error appears in the above-identified patent and that said Letters Patent is hereby corrected as shown below:

On title page, item 75 Inventors
  replace "Eric Romera, Kraainhem"
  with --Eric Romers, Kraainem--.

Signed and Sealed this

Thirty-first Day of August, 1999

Attest:

Q. TODD DICKINSON

*Attesting Officer*  *Acting Commissioner of Patents and Trademarks*